United States Patent [19]

Stewart, Jr. et al.

[11] Patent Number: 5,637,094
[45] Date of Patent: Jun. 10, 1997

[54] MULTIPLE DOSAGE SYRINGE

[75] Inventors: Edward Stewart, Jr.; Edward Stewart, Sr., both of Dodge City, Kans.

[73] Assignee: Pos-T-Vac, Inc., Dodge City, Kans.

[21] Appl. No.: 334,757

[22] Filed: Nov. 4, 1994

[51] Int. Cl.$^6$ .................................................. A61M 5/20
[52] U.S. Cl. ........................... 604/135; 604/136; 604/157
[58] Field of Search .................................. 604/134, 135, 604/136, 137, 138, 139, 157

[56] References Cited

U.S. PATENT DOCUMENTS

| | | | |
|---|---|---|---|
| 2,585,815 | 2/1952 | McLintock . | |
| 2,695,023 | 11/1954 | Brown . | |
| 3,880,163 | 4/1975 | Ritterskamp | 604/136 |
| 4,150,669 | 4/1979 | Latorre . | |
| 4,592,745 | 6/1986 | Rex et al. . | |
| 5,114,406 | 5/1992 | Gabriel et al. | 604/136 |
| 5,137,516 | 8/1992 | Rand et al. | 604/136 |
| 5,358,489 | 10/1994 | Wyrick | 604/136 |
| 5,425,715 | 6/1995 | Dalling | 604/136 |

OTHER PUBLICATIONS

Photocopy of container for "Autopen AN 3000" by Owen Mumford Brochure by Medis entitled Painpen.

*Primary Examiner*—Todd E. Manahan
*Attorney, Agent, or Firm*—Hovey, Williams, Timmons & Collins

[57] ABSTRACT

A syringe is provided for injecting multiple sequential dosages of a liquid medicine includes a single actuator for initiating a penetration and injection sequence. The syringe hereof is adjustable for different dosages while providing for physical selection of a desired, predetermined dosage. The syringe includes a retraction mechanism for withdrawing the needle into a protective collar after administration of the dosage. The syringe receives a vial for administering multiple dosages without the necessity of replacing the vial after each administration.

16 Claims, 3 Drawing Sheets

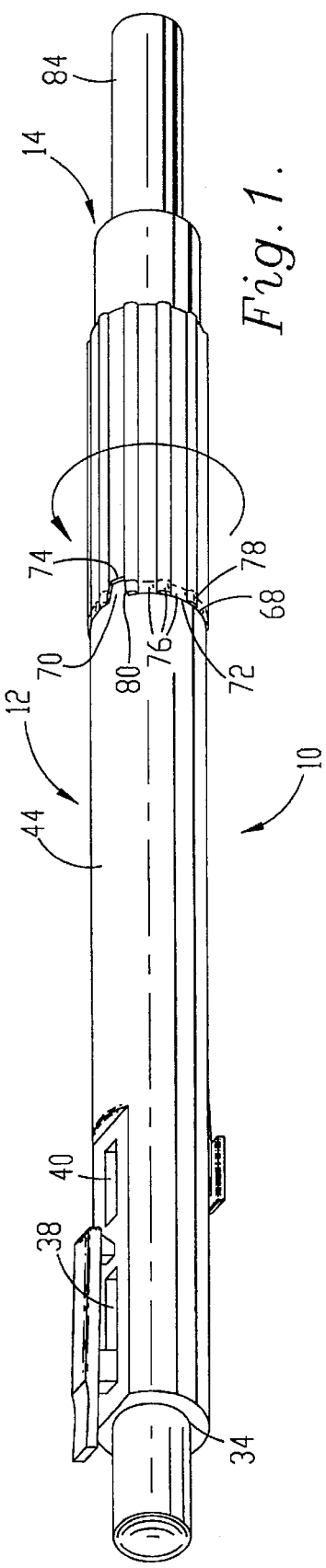
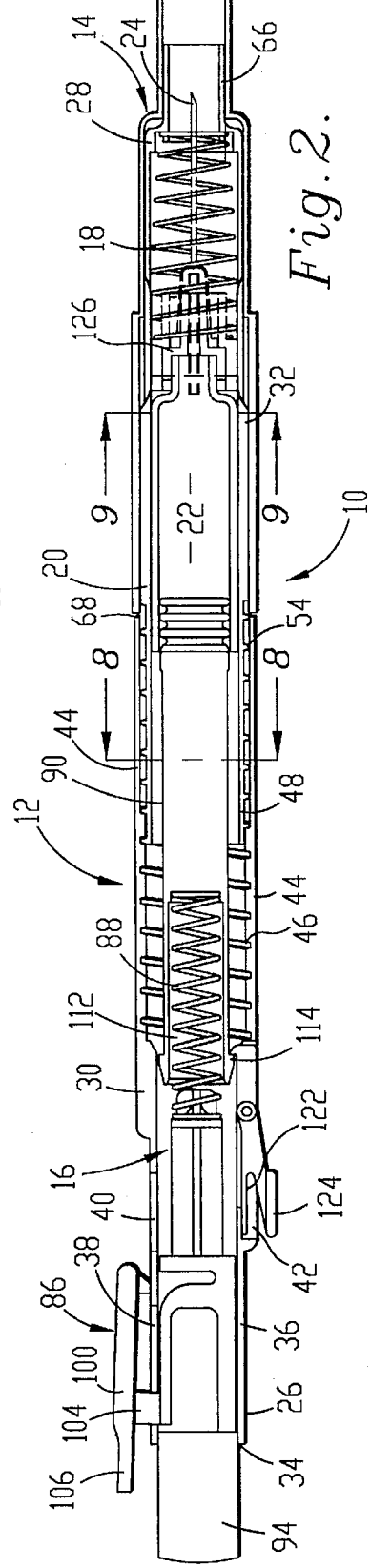
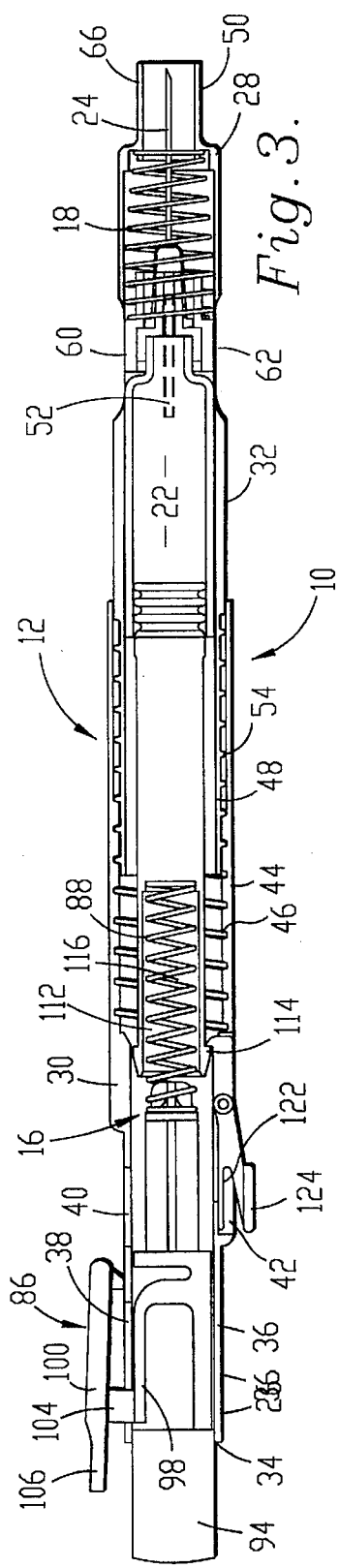

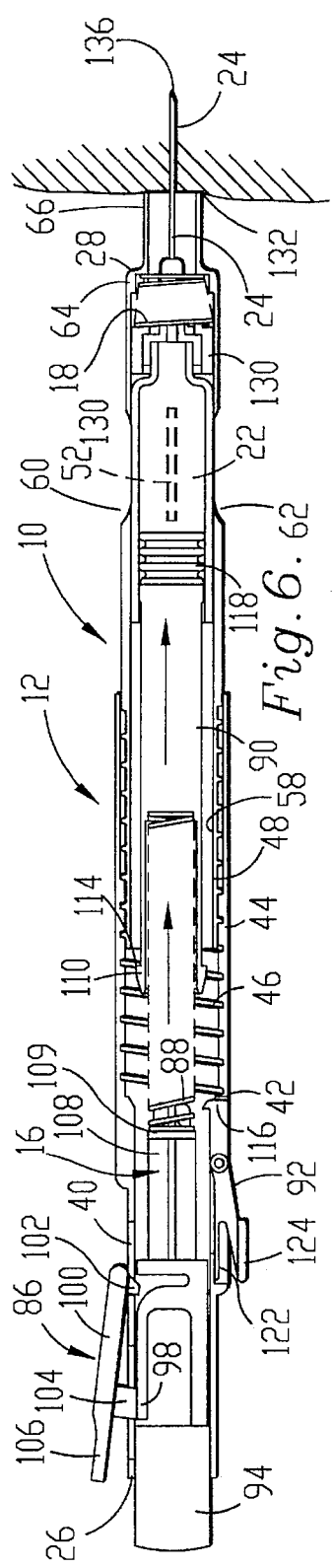
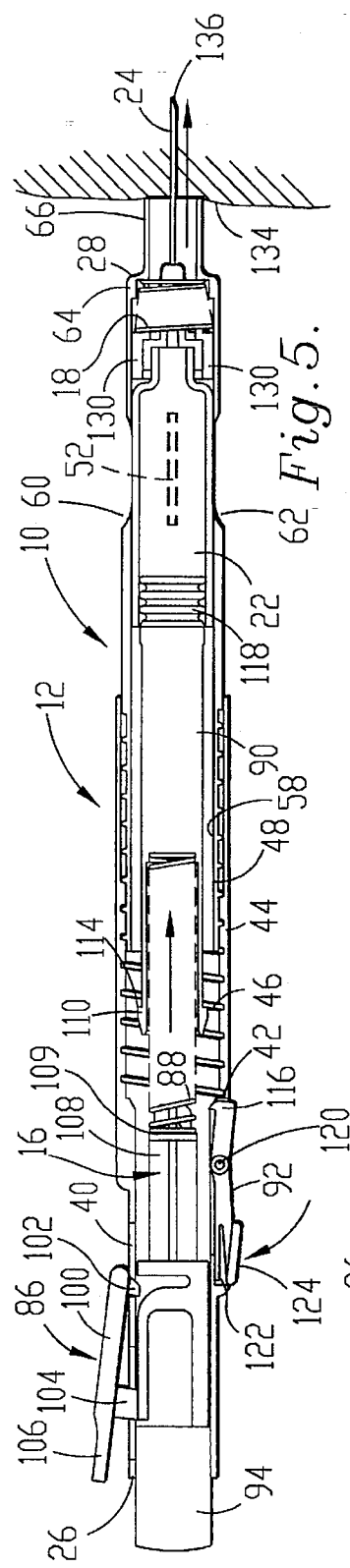
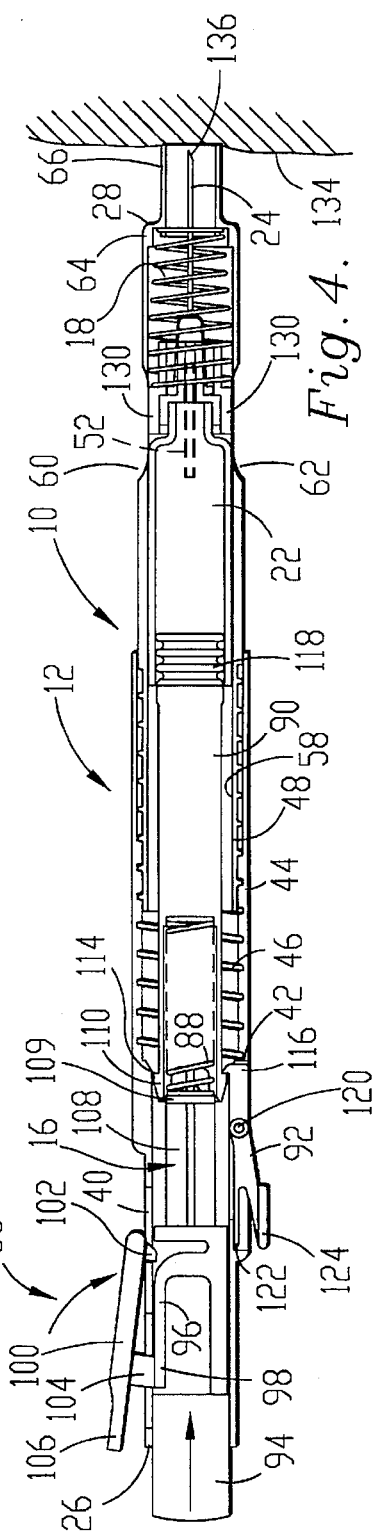

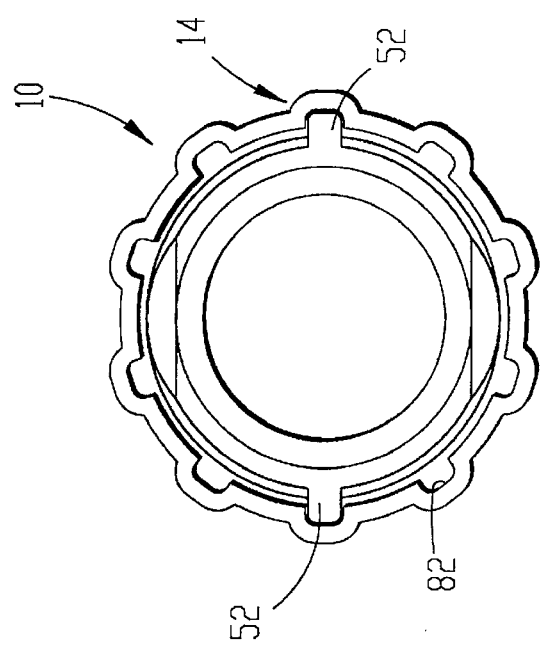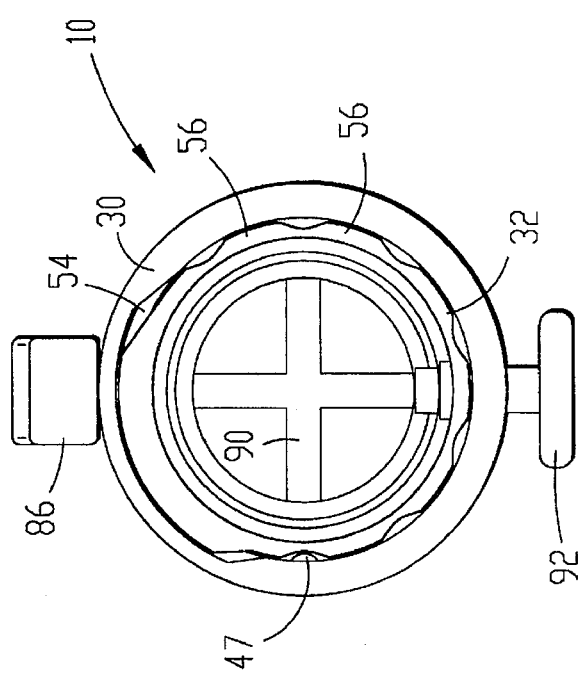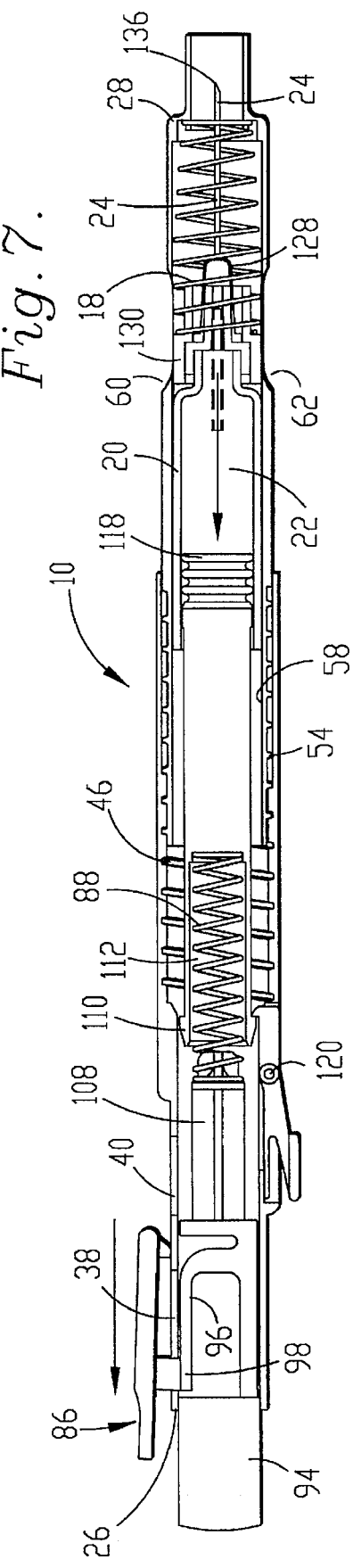

MULTIPLE DOSAGE SYRINGE

BACKGROUND OF THE INVENTION

1. Field of the Invention

This invention broadly concerns a multiple dosage syringe for administering selectable amounts of medication through a cannula. More particularly, the invention hereof permits the user to position the syringe in place before triggering the syringe to self-penetrate the skin and inject the medication.

2. Description of the Prior Art

Male impotence is a problem which is more often encountered upon aging, with geriatric patients comprising a significant if not majority of the patients. The treatment of male impotence has heretofore involved three principle areas other than psychiatric intervention. One method of treatment has involved penile implants. These have met with increased patient and physician resistance due to occasional rejection by the patient's body, the possibility of infection, and the need for the passage of a tube through the patient's skin on a permanent basis, coupled with the possibility of rupture of the implant. Another type of treatment which has been employed is vacuum therapy, where the patient places his penis in a tube and withdraws air to create a vacuum. The vacuum causes blood to flow into the penis and once rigidity is attained, a constrictor ring is placed around the penis to maintain rigidity until intercourse is complete. However, the vacuum devices may be bulky and the constriction rings uncomfortable, coupled with their tourniquet-like effects which require removal after a short period.

A third type of treatment being employed on a limited basis involves injection of a vasodilator such as Prostaglandin sold by The Upjohn Company, into the penis prior to intercourse to induce engorgement of the penis with blood. This method, described in U.S. Pat. No. 4,127,118 to Latorre, is gaining popularity, but presents two distinct disadvantages. One is the necessity for datermining a desired dosage for each patient. Because the patients differ in weight, the amount of vasodilator to be injected is variable, and often individual syringes must be preloaded by a physician or pharmacist prior to use. The physical ability and memory of a patient often makes it difficult for each patient to load his own syringe from a more economical vial. The second problem involves the difficulty of the patient in selecting the correct location for injection of the vasodilator into the flaccid penis, coupled with the reluctance of the patient to physically insert the needle or cannula through the skin and into the penis.

It is thus an object of this invention to provide a syringe which is capable of injecting multiple doses of a medication.

It is another object of this invention to provide a syringe with an auto-inject feature which will permit patient placement of the syringe without a projecting cannula.

It is another object of this invention to provide a syringe which will penetrate the patient's skin and inject a dose of medication in response to activation of a trigger mechanism.

It is another object of this invention to provide a syringe which will retract the needle after use.

it is another object of this invention to provide a syringe capable of adjustment to provide different dosages.

It is another object of this invention to provide a syringe which is provided with a tactile, positive indicator whereby the patient can readily ascertain when the syringe has been set for a predetermined dosage of medication.

It is a further object of the invention to provide a mechanism whereby the pharmacist or physician can set the tactile, positive indicator for one of a number of different dosages.

It is yet further object of the invention to provide a multiple dosage syringe having a compact and portable configuration which is easy to use for geriatric patients.

SUMMARY OF THE INVENTION

These and other objects are successfully met by the present invention which may be used not only in the treatment of male impotence but also in the administration of medication for other conditions or diseases where self-administration of multiple injections are required. The multiple dosage syringe hereof is designed to carry a vial capable of carrying multiple dosages of a liquid medication and mounting replaceable cannulae. The syringe is also preferably provided with a trigger whereby the user may administer a desired dosage automatically.

The multiple dosage syringe hereof broadly includes a syringe body defining an interior cavity which is adapted to receive a vial containing liquid medication therein. The vial is preferably carried within the body for shiftable movement therealong and mounts a cannula such as a needle at a remote end. The opposite end of the vial includes a stopper which is engaged by a plunger. An advancing spring within the body moves the plunger into the stopper to expel medication from the cannula. Preferably, the advancing spring also serves to move the vial along the longitudinal axis of the cavity so that the cannula then projects from the remote end.

Preferably, the multiple dosage syringe may be adjusted to a desired dosage. This may be accomplished in the present invention by a two-part body, the lower section of the body being threadably engaged with the upper section. By turning the lower section relative to the upper section, the amount of travel of the advancing spring is reduced upon full extension, so that after cocking, in order to achieve full spring extension, the advancing spring must move the stopper to expel the liquid medication corresponding to the desired dosage. The frictional engagement between the stopper and wall of the vial is greater than the strength of the return spring so that when the syringe is adjusted to a desired dosage, cocked, and the trigger actuated, the advancing spring moves the vial forward until the return spring is fully compressed. The advancing spring is strong enough to overcome the friction between the stopper and the wall of the vial so that after the return spring is fully compressed, the advancing spring moves the stopper forward until fully extended and the desired dosage is expelled through the cannula. A detent is provided between the upper and lower sections of the body whereby a positive tactile indication is provided to the user when the dosage amount is set.

In particularly preferred embodiments, the syringe hereof is provided with a means of establishing a desired predetermined dosage by the user independent of visual indicators, and most preferably this setting may be varied. This may be accomplished by, for example, a removable cover which is provided with a notch in the upper margin. The cover preferably engages with the lower section to turn therewith and is complementally configured to mate with a tooth projecting from the lower margin of the upper section. The circumferential duration of the notched portion of the cover may be varied by the physician or pharmacist removing discrete portions. Thus, the cover and the lower section may be turned relative to the upper section to select and load the syringe for a particular dosage which is felt and seen by the patient when the tooth engages the shoulder of the notch.

The invention preferably provides an automatic injection feature including a protective collar which surrounds the needle prior to administration of the dosage. The collar provides not only a protection against premature pricking of the skin and consequently aids the user in permitting proper placement of the device, but also assists by enabling insertion of the needle to the proper depth. By employing a triggered insertion of the cannula and subsequent administration of the dosage, injection is readily and more accurately accomplished.

By also providing a retraction spring for returning the vial to its original position, the multiple dosage syringe provides both adjustable dosages, automatic insertion, and compact storage for administration of subsequent doses. The same syringe can be repeatedly used with mere substitution of new cannula, which are attached before each administration to a locking hub on the vial. Compact storage is especially a concern in the treatment of male impotency where transportation and privacy in administration are a concern.

These and other features of the present invention are disclosed as set forth in the following drawings and detailed description.

BRIEF DESCRIPTION OF THE DRAWINGS

FIG. 1 is a perspective view of the multiple dosage syringe of the present invention with the cover in position and an arrow depicting the rotation of the cover to preload a desired dosage;

FIG. 2 is a vertical cross-sectional view of the syringe hereof with the cover in position for rotating the lower section of the body relative to the upper section to preload the syringe with a desired dosage;

FIG. 3 is a vertical cross-sectional view similar to FIG. 2 with the cover removed and showing the lower section threadably advanced onto the upper section to compress the advancing spring corresponding to a desired dosage;

FIG. 4 is a vertical cross-sectional view similar to FIG. 3 but showing the cocking button depressed prior to insertion of the cannula through the patient's skin;

FIG. 5 is a vertical cross-sectional view similar to FIG. 4 and showing the trigger depressed to advance the vial and cannula toward the remote end of the syringe body;

FIG. 6 is a vertical cross-sectional view similar to FIG. 5 and showing the cannula at full penetration with the advancing spring pushing on the stopper of the vial to dispense medication therefrom;

FIG. 7 is a vertical cross-sectional view similar to FIG. 6 but showing the release lever depressed allowing the return spring to withdraw the vial proximately into the cavity of the syringe body;

FIG. 8 is an enlarged vertical cross-sectional view taken along line 8—8 of FIG. 2 showing the detent and spline arrangement between the lower and upper body sections; and FIG. 9 is an enlarged vertical cross-sectional view taken along line 9—9 of FIG. 2 showing the interlocking engagement between the cover and the lower body section and the vial positioned within the lower body section.

DESCRIPTION OF THE PREFERRED EMBODIMENT

Referring now to the drawing, a multiple dosage syringe 10 in accordance with the present invention is shown in FIGS. 1–9 and broadly includes a substantially tubular body 12, a cover 14, a penetrating and dispensing mechanism 16, and a return spring 18. The syringe 10 is adapted to receive a vial 20 containing liquid medication such as a vasodilator therein, although other types of liquid medication 22 such as insulin, etc. which may be self-administered are equally applicable. A cannula 24 such as a hypodermic needle is mountable on the vial 20 for injecting a desired quantity of the liquid medication 22 into the patient.

In greater detail, the body 12 of the syringe 10 presents a proximate end 26 away from the skin to be penetrated and a remote end 28 to be positioned on the skin to be penetrated. The body 12 is preferably made of a suitable synthetic resin material and molded into an upper section 30 and a lower section 32 which are threadably interfitted. The upper section 30 includes a proximate end 26 which includes an axially aligned opening 34 and presents a sidewall 36 including slot 38 and hole 40 aligned therewith. The proximate end 26 also includes a gap 42 through the sidewall 36 opposite the slot 38. The upper section 30 also includes a distal portion 44 which includes internal thread 46 integrally molded therein. Also molded into inside of the distal portion 44 is a detent 47 as shown in FIG. 8.

The lower section 32 presents threaded section 48 for interengagement with the distal portion 44 and a remote section 50 through which the cannula 24 is attached and removed. The threaded section 48 presents a pair of exposed, radially extending fins 52 best seen in FIG. 9 and shown in phantom in FIGS. 2–7. The threaded section, while generally cylindrical, also presents an external thread 54 for interengagement with the internal thread 46. Further, as shown in FIG. 8, the threaded section 48 also includes a plurality of longitudinally extending splines 56 over which the external thread 54 extends, the splines 56 engaging with the detent 47 to provide a positive feel and clicking sound as each spline 56 is engaged by the detent 47 during threading of the lower section 32 onto the upper section 30. The internal surface 58 of the lower section 32 along the threaded section 48 presents a smooth bore to permit axial shifting of the vial 20 along an axis generally defined by the cannula 24.

Opposed relieved areas 60 and 62 are provided in the lower section whereby a vial 20 is exposed to visual inspection while retained in the bore defined by the internal surface 58. Located remotely from the relieved areas 60 and 62 is nose piece 64 which presents a collar 66 for surrounding the cannula and protecting the patient from uncomfortable skin pricks prior to insertion. The nose piece 64 may be made separately from the rest of the lower section 32 and glued in place for ease of manufacturing. The collar 66 is of sufficient length to protect the skin notwithstanding axial movement of the vial 20 and cannula 24 during selection of the dosage and preloading of the penetrating and dispensing mechanism 16.

The upper section 30 also presents a distal margin 68 including a tooth 70 which projects therefrom. The cover 14 includes an edge 72 which includes a notch 74 complementally sized to receive tooth 70 therein. Extending circumferentially from the notch 74 around the edge 72 are a plurality of removable tabs 76 which are separable along score lines, perforations or other lines of weakening 78 from the adjacent tabs 76 and the remainder of the cover 14. Each tab 76, when removed, leaves a shoulder 80 on the remaining tab previously adjacent thereto, of a depth less than that of notch 74 but which nonetheless provides both a positive visual and tactile indication of engagement with the tooth 70, the depth of each shoulder being about ¾ that of the depth of the notch 74. Removal of one or a plurality of tabs 76 defines the dosage which is set by rotating the cover 14 and the lower section 32 relative to the upper section 30. The cover 14 presents a plurality of internal grooves 82 which receive the fins 52 for positive interengagement during rotation, as best seen in FIG. 9. The cover 14 also includes an elongated cap 84 for inhibiting foreign particles from contacting the cannula 24 when the latter is mounted on the vial 20.

The penetrating and dispensing mechanism 16 broadly includes the thumb button 86, the advancing spring 88, the plunger 90 and the trigger button 92. The thumb button 86 is preferably molded in a single piece of resilient synthetic resin material and includes head 94 projecting proximately through opening 26, carrier section 96 which slides longitudinally within upper section 30 and includes arm 98, and latch 1 00 which includes finger 102. The arm 98 is connected to the latch 1 00 by bridge 104 which moves along slot 38 when the head 94 is depressed or the vial 20 is returned to its unloaded condition by return spring 18. The finger 102 serves to engage the part of the sidewall 36 surrounding the hole 40 when the head 94 is fully depressed. The arm 98 normally biases the finger 102 to a position within the hole 40 to hold the thumb button 86 in a relatively remote position; depressing the thumbrest 106 on the latch 100 causes the bridge 104 to act as a fulcrum and disengage the finger 102 from the hole 40.

The head 94 also presents a stem 108 which projects remotely from the carrier section 96 and is preferably, though not necessarily, cruciform in cross-section. The stem presents a disc 109 of almost the same diameter as the interior diameter of the plunger 90 to act as a guide and also to engage the advancing spring 88. While other spring configurations can be used, a single helix steel spring is most economical and efficient for the present application. The advancing spring 88 has a sufficient spring co-efficient of strength to cause the vial and cannula to advance longitudinally, cause the cannula 24 to penetrate the patient's skin to the desired depth, and relatively quickly push on the vial 20 to dispense the desired dosage as the advancing spring relaxes to full extension. The advancing spring 88 is also of a sufficient diameter to fit within the plunger 90. The proximate end of the advancing spring 88 engages the disc 108 while the remote end of the advancing spring 88 engages the plunger 90.

The plunger 90 presents a tapering shoulder 110 around the opening into the cavity 112 at its proximate end. The cavity 112 is sized to receive the advancing spring 88 and the stem 108 therein as shown in FIG. 4. The tapering shoulder 110 includes a sharp corner 114, so that the catch 116 on trigger button 92 can hold the plunger 90 to retain the advancing spring 88 in a compressed condition. The plunger 90 also includes a push rod which extends proximately to engage the stopper 118 in the large end of the vial 20.

The trigger button 92 includes laterally projecting nibs 120 which enter corresponding holes in the gap 42 of the upper section 30 so that the nibs 120 act as pivot points. The trigger button includes a resilient leg 122 which resists depression of the key 124 and biases the catch 116 toward and into engagement with the shoulder 110. The remote surface of the catch 116 is rounded to ride over the shoulder 110 until the catch 116 moves over the corner 114.

The vial 20 used in the present invention is of glass or synthetic resin and shiftably and sealingly receives stopper 118 in its larger open second end after filling. The stopper 118 is configured complementally with the plunger 90 to hold the latter in position during use. The narrow and remote first end of the vial is provided with a conventional tip 126 with a self-sealing membrane and a Luer lock fitting to receive the cannula 24. The cannula includes a hub 128 for mounting to the Luer lock connection on the tip 126.

An adaptive rim 130 is provided for positioning over the tip 126 of the vial 20 to engage the return spring 18. The return spring is positioned between the nose piece 64 and the adaptive rim 128 and is of a spring steel material with a lesser strength than the advancing spring 88. In fact, it is desirable that the return spring 18 be of relatively little strength so as to provide minimum resistance to advancing spring 88, yet of sufficient resiliency to withdraw the vial 20 and a cannula 24 mounted thereon after administration of the dose.

The use of the present invention is described with reference to treatment of male impotence. While the invention hereof particularly addresses many of the problems presented by injection therapy of that condition, it may be recognized that the present invention is not limited in usage to injections for that purpose.

Prior to use, a vial 20 containing multiple doses of medication 22 such as Prostaglandin, is provided with the adaptive rim 130 placed over its tip 126, which is oriented toward the return spring 18. The return spring 18 is positioned within the lower section 32 of the body 12 adjacent the remote end. A cannula 24 is locked onto the vial 20. The dosage prescribed by the physician is set by the pharmacist by removing a desired number of tabs from the cover. For example, the threads of the upper and lower section and the sizing of the tabs could correspond to permit removal of each tab equal to one-tenth cubic centimeter (0.1 cc). It may be readily apparent that other volumes could be provided depending on the pitch of the threads and the size of the tab 76 to be removed. Under the assumption, if the pharmacist wanted to set the dosage to 0.5 cc's, then five tabs would be removed. In the present invention, the dosage would be presettable for male impotence treatment between about 0.1 and 0.8 cc's, although wider ranges could readily be accommodated. Under the dosage volumes just described, the typical vial would contain about 10 cc's of medication.

After removing the tabs 76, the cover 14 is placed over the body 12 with the notch 74 aligned with the tooth 70 and the grooves 82 receiving the fins 52. The notch and tooth alignment provides a zero setting for dosage selection prior to each administration. The syringe 10 is then ready for use by the patient. When the patient desires to use the syringe 1 0, the cover 14 is rotated in the clockwise direction as indicated by the arrow in FIG. I until the tooth 70 engages the shoulder 80 on the cover 14 determined by the first tab 76 not removed. As the patient rotates the cover 14 and the lower section 32 carried thereby relative to the upper section 30, the detent 47 clicks against the splines 56 to provide a further indication of the dosage being set, and the return spring compresses. FIG. 2 shows the syringe 10 hereof prior to rotation of the cover 14 and lower section 32, while FIG. 3 shows the syringe after dosage setting and with the cover removed. The rotation of the lower section 32 into the upper section causes a forward movement of the vial 20 to compress the return spring 18 because it is weaker than the advancing spring 88. When the tooth 70 engages the shoulder 80, the proper dosage has been set and the cover removed.

The head 94 of the thumb button 86 is depress to load the advancing spring 88 and make the syringe ready for an injection. The catch 116 holds the plunger 90 and compresses the advancing spring 88 between the plunger and the thumb button 86 which is held by the finger in the hole 40. The arrows in FIG. 4 illustrate the movement of the finger 102 into the hole 40 when the bridge 104 moves along the slot 38 responsive to depressing the head 94. The syringe 10 is positioned with the remote margin 132 of the collar 66 placed against the target area of the patient's skin 134. In the treatment of male impotence, the desired target is near the base of the penis with insertion into the corpora spongiosim desired. It may be appreciated from FIG. 4 that in this condition, the patient feels only the collar 66 and not the undesired sharpness of the point of 136 of the cannula 24 while positioning the syringe 10 over the target area.

To administer the dosage, the patient pushes on the key 124 of the trigger button 92 as indicated by the arrow in FIG. 5. This causes the catch 116 to move off the corner 114 and the advancing spring 88 expands. As the spring 88 expands, the return spring 18 becomes fully compressed as the cannula penetrates the patients skin to the desired depth. Once the return spring is fully compressed, the advancing spring 88 pushes against the stopper 118. Because the return spring 18 prevents the vial 20 from moving remotely, the stopper moves responsively to the biasing force of the advancing spring 88 pushing on the plunger 90 and shifts toward the first end of the vial 20 which carries the tip 126, causing a desired dosage of the medication 22 to be expelled from the cannula and injected into the patient. FIG. 6 illustrates the movement of the stopper 118 after the return spring 18 is fully compressed in FIG. 5.

After the dosage is fully administered as shown in FIG. 6, the cannula 24 is replaced on the tip 126 of the vial prior to retracting the vial 20 fully. The lower body section 32 is then rotated slightly relative to the upper body section 30 to "burp" the air out of the cannula and make the syringe ready for the next injection. The thumbrest 106 is depressed to permit the return spring 18 to expand and push the vial 20, plunger 90, advancing spring 88 and thumb button 86 proximately as shown in FIG. 7. The syringe 10 is then ready for administration of the next dosage. The patient can look at the vial 20 adjacent the relieved areas 60 and 62 to monitor the amount of medication 22 remaining in the vial 20 so that he may know when to replace the vial. The cover 14 is placed over the body 12 with the tooth 70 in alignment with the notch 74 to define a new zero point for setting the next desired dosage.

A predetermined dosage may be readily identified, prescribed, and administered as set forth herein. Further, the patient may adjust the dosage by a fewer or greater number of "clicks" or tabs 76, if desired in a particular circumstance. But advantageously, a forgetful patient will have a ready and easily determined dosage reference which he can set and administer. The autoinject feature of the present invention, coupled with the shielded cannula point, may assist patients who have difficulty in physically locating and pushing the needle through sensitive skin. Finally, the withdrawal of the cannula back into the body provides enhanced safety and portability of the device hereof. With these considerations in mind, the present invention presents a marked improvement on existing multiple injection devices.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby states their intent to rely on the Doctrine of Equivalents to determine and assess the reasonably fair scope of their invention as pertains to any apparatus not materially departing from but outside the liberal scope of the invention as set out in the following claims.

We claim:

1. A syringe comprising:

a syringe body including an upper section and a lower section shiftably intercoupled for changing the length of said body, said body having a longitudinal axis, said lower section presenting a remote end for positioning adjacent a patient's body, said syringe body including a lower section and an upper section threadably interconnected, at least one of said lower and upper sections including a detent for engaging the other of said sections during relative rotation of the upper and lower sections the other of said sections including a plurality of splines extending longitudinally along said threads in said other section for engaging the detent during relative rotation of the upper and lower sections;

a vial of liquid medicament shiftably received with said body for movement along said axis, said vial presenting opposed first and second vial ends, said first vial presenting structure for mounting a cannula thereon, said second end receiving a stopper enclosing said second end and shiftably received within said vial;

a cannula mounted on said first vial end;

a plunger positioned in said body in abutment with said stopper;

an advancing spring positioned in said syringe body and operatively connected to said vial and said plunger for translating said vial longitudinally within said body and shifting said stopper within said vial;

an arming actuator shiftably mounted to and including a head projecting externally from said upper section of said body for loading said advancing spring; and a trigger operatively connecting said body and said vial, said trigger being shiftably carried by said upper section for movement between a first position in engagement with said plunger or operatively retaining said vial in a pre-injection projection with said advancing spring in a loaded condition and a second releasing position disengaged from said plunger for permitting said advancing spring to shift said vial longitudinally along said syringe body toward said remote end into a medicament discharging position.

2. A syringe as set forth in claim 1 including a retracting spring positioned within said body for compression responsive to shifting of said vial toward said remote end.

3. A syringe as set forth in claim 2 wherein said arming actuator includes means for selectively permitting said retracting spring to expand after compression to shift said vial and translate said advancing spring away from said remote end.

4. A syringe as set forth in claim 1 wherein said arming actuator includes structure for engaging said body to hold said arming actuator in a position compressing said advancing spring between said arming actuator and said plunger.

5. A syringe as set forth in claim 1 wherein said arming actuator includes a latch for releasing said engaging structure to permit axial shifting of said arming actuator.

6. A syringe as set forth in claim 1 wherein said cannula presents a point oriented toward said remote end, said point being positioned within said body when said vial is in said preinjection position and being positioned externally of said body when said vial is shifted into said medicament discharging position.

7. A syringe as set forth in claim 1 wherein said trigger is pivotally mounted to said body.

8. A medical injection device for receiving a vial and a cannula, said injection device comprising:

a syringe body for receiving a vial containing multiple dosages of a medicament, said body including an upper section presenting a proximate end and a lower section threadably interengaged with said upper section for varying the effective length of the body, said lower section including a remote end, said upper section including an externally positioned engagement member thereon;

means for shifting the vial axially within said receiving means between a first position with the cannula enclosed by said receiving means and a second position with the cannula projecting from said remote end of said receiving means;

means for adjustably selecting a desired dosage to be administered, said dosage selecting means including a cover mounted on said lower section for rotation therewith during relative movement between said upper and lower sections, said cover presenting a shoulder, said shoulder being positioned for enfiagement with said engagement member upon rotation of said cover and lower section relative to said upper section to define a desired dosage; and means for selectively actuating said shifting means.

9. A medical injection device as set forth in claim 8 wherein said shifting means includes advancing means for shifting said vial with sufficient force to cause said cannula to penetrate human skin.

10. A medical injection device as set forth in claim 8 including means for shifting said vial from said second position back to said first position.

11. A medical injection device as set forth in claim 8 wherein said dosage selection means includes means for indicating a desired dosage among a plurality of possible dosages.

12. A medical injection device as set forth in claim 11 wherein said indicating means includes abutment structure for indicating a predetermined desired dosage.

13. A medical injection device as set forth in claim 8 wherein said shifting means includes a spring and said actuating means includes means for loading said spring and retaining said spring in a loaded condition.

14. A medical injection device as set forth in claim 13 wherein said actuating means further includes a trigger for rapidly releasing said spring from a loaded condition to thereby axially shift the vial.

15. A medical injection device as set forth in claim 8 wherein said receiving means includes means for ascertaining when the quantity of medicament contained in the vial is exhausted prior to administration of the last dosage of medicament therefrom.

16. A medical injection device as set forth in claim 8, wherein said cover includes a plurality of tabs removable along lines of weakening, removal of each tab presenting a respective shoulder corresponding to a different selected dosage.

* * * * *